United States Patent [19]
Walker et al.

[11] Patent Number: 5,320,604
[45] Date of Patent: Jun. 14, 1994

[54] LOW-PROFILE SINGLE-LUMEN DUAL-BALLOON CATHETER WITH INTEGRATED GUIDE WIRE FOR EMBOLECTOMY DILATATION/OCCLUSION AND DELIVERY OF TREATMENT FLUID

[75] Inventors: Blair D. Walker, Long Beach; Sheryl W. Higgins, Silverado, both of Calif.

[73] Assignee: Baxter International Inc., Deerfield, Ill.

[21] Appl. No.: 71,731

[22] Filed: Jun. 3, 1993

Related U.S. Application Data

[63] Continuation-in-part of Ser. No. 970,581, Oct. 22, 1992, which is a continuation of Ser. No. 690,447, Apr. 24, 1991, abandoned.

[51] Int. Cl.$^5$ .............................................. A61M 29/00
[52] U.S. Cl. ........................................ 604/96; 604/101
[58] Field of Search ............... 604/96, 95, 101, 49–54, 604/264, 280, 169, 170, 164; 606/191–195

[56] References Cited

U.S. PATENT DOCUMENTS

| | | |
|---|---|---|
| 4,636,195 | 1/1987 | Wolinsky . |
| 4,763,654 | 8/1988 | Jang ................... 604/101 X |
| 4,983,167 | 1/1991 | Sahota ................... 606/194 |
| 4,988,356 | 1/1991 | Crittenden et al. ........... 604/96 X |
| 4,994,033 | 2/1991 | Shockey et al. . |
| 5,002,532 | 3/1991 | Gaiser et al. . |
| 5,049,132 | 9/1991 | Shaffer et al. . |
| 5,071,406 | 12/1991 | Jang ....................... 604/96 |
| 5,102,390 | 4/1992 | Crittenden et al., . |
| 5,129,883 | 7/1992 | Black . |
| 5,163,906 | 11/1992 | Ahmadi . |
| 5,171,221 | 12/1992 | Sampson . |
| 5,171,222 | 12/1992 | Euteneuer . |

FOREIGN PATENT DOCUMENTS

| | | |
|---|---|---|
| 1553915 | 6/1976 | |
| 0080436 | 6/1983 | European Pat. Off. . |
| 277367 | 8/1988 | European Pat. Off. . |
| 277370 | 8/1988 | European Pat. Off. . |
| 427429 | of 1989 | European Pat. Off. . |
| 474906 | 1/1989 | European Pat. Off. . |
| 399712 | 5/1989 | European Pat. Off. . |
| 362146 | 4/1990 | European Pat. Off. . |
| 364799 | 4/1990 | European Pat. Off. . |
| 2834956 | 8/1978 | Fed. Rep. of Germany . |
| 3616205 | 5/1986 | Fed. Rep. of Germany . |
| 3915289 | 5/1989 | Fed. Rep. of Germany . |
| 3833359 | 4/1990 | Fed. Rep. of Germany . |
| 4001086 | 7/1991 | Fed. Rep. of Germany . |
| 2350849 | 5/1976 | France . |
| 2600205 | 5/1987 | France . |
| 11426278 | 4/1972 | United Kingdom . |
| 2043449 | 10/1980 | United Kingdom . |
| 2187390 | 9/1987 | United Kingdom . |
| WO82/0333 | 10/1982 | World Int. Prop. O. . |
| WO84/01514 | 4/1984 | World Int. Prop. O. . |
| WO88/03389 | 5/1988 | World Int. Prop. O. . |
| WO89/00829 | 2/1989 | World Int. Prop. O. . |
| WO89/07413 | 8/1989 | World Int. Prop. O. . |
| WO90/07352 | 7/1990 | World Int. Prop. O. . |
| WO91/12846 | 9/1991 | World Int. Prop. O. . |
| WO91/19528 | 12/1991 | World Int. Prop. O. . |

*Primary Examiner*—John D. Yasko
*Attorney, Agent, or Firm*—Poms, Smith, Lande & Rose

[57] ABSTRACT

A fully exchangeable low-profile single-lumen dual-balloon catheter for embolectomy, dilatation, occlusion, and infusion of treatment fluid, and having an integrated guide wire, includes a flexible small diameter guide wire provided with an distal end valving portion of comparatively enlarged diameter and a flexible elongated tubular shaft with a pair of expandable balloons spaced apart on opposite sides of a waist portion which waist portion includes an infusion section with a perforation in fluid communication with the lumen. The fluid conducting lumen is adapted to perform multiple functions in conjunction with movements of the guide wire converting the catheter to one of several modes of operation by sealing cooperation of the guide wire valving portion with seal portions of the catheter shaft.

21 Claims, 4 Drawing Sheets

Fig. 7

LOW-PROFILE SINGLE-LUMEN DUAL-BALLOON CATHETER WITH INTEGRATED GUIDE WIRE FOR EMBOLECTOMY DILATATION/OCCLUSION AND DELIVERY OF TREATMENT FLUID

RELATED CASES

This application is a continuation-in-part of U.S. application Ser. No. 07/970,581, filed on Oct. 22, 1992, which is a continuation of U.S. application Ser. No. 07/690,447, filed on Apr. 24, 1991, which is now abandoned.

FIELD OF THE INVENTION

The present invention relates in general to the field of dilatation or balloon catheters employed in the treatment of vascular diseases. More particularly, the present invention relates to a single-lumen low-profile integrated or fixed-wire balloon catheter assembly with two spaced apart balloon sections which can be positioned quickly and easily for use in removing an embolus or opening vascular stenoses using a dilatation balloon of the catheter. Also, the present catheter allows a second occlusion balloon to be used in conjunction with the dilatation balloon which itself is functioning in an occlusion mode to define an intravascular chamber into which therapeutic materials, such as plaque solubilizing liquids and lesion treatment drugs, may be delivered via the single lumen and an infusion section of the catheter. Additionally, the present catheter provides the advantages of rapid balloon removal and replacement while retaining the guide wire in place for easy access to the stenotic lesion.

BACKGROUND OF THE INVENTION

Over the last decade the medical procedure known as angioplasty has become widely accepted as a safe and effective method for treating various types of vascular diseases. For example, angioplasty is widely used for opening stenoses throughout the vascular system and particularly for opening stenoses in coronary arteries. At present, the most common form of angioplasty is called percutaneous transluminal coronary angioplasty (PTCA). This procedure utilizes a dilatation catheter having an inflatable balloon at its distal end. In a procedure using a fluoroscope and radiopaque dyes for visualization the distal end of the dilatation catheter is guided into position through a guide catheter and across the stenosis. With the dilatation balloon in this position of alignment with the stenosis the balloon is inflated for a brief duration to open the artery and establish adequate blood flow.

An alternative procedure for opening blocked or constricted vascular pathways or analogous physical structures utilizes a similar balloon catheter to remove the blockage or embolus by advancing the deflated balloon of the catheter past the blockage, inflating the balloon and then withdrawing the catheter. By withdrawing the inflated balloon the downstream embolus is pulled or stripped from its location and ultimately removed.

Typically, inflation of the balloon is accomplished by supplying pressurized fluid from an inflation apparatus located outside the patient's body through an inflation lumen in the catheter which is connected to the balloon. Conversely, applying a negative pressure to the inflation lumen collapses the balloon to its minimum dimension for initial placement or removal of the balloon catheter within the blood vessel receiving treatment.

In the past years a number of balloon catheter designs have been developed which have contributed to the safety and acceptability of PTCA and similar medical procedures. The most common design is known as an "over-the-wire" balloon catheter. This conventional device typically utilizes a relatively large lumen for passage of a guide wire and injection of contrast fluid (or angiographic visualization dye) to assist in the placement of the device. A second parallel lumen is provided for inflation and deflation of the balloon.

Typically, a steerable guide wire is positioned within the larger lumen and the entire assembly is maneuvered into an initial position within the target artery through a guide catheter which has been positioned previously, and is of sufficient diameter to pass the angioplasty catheter. Once near the site of the stenoses the guide wire can be rotated and axially extended or retracted into position across the lesion. The catheter is subsequently advanced along the guide wire to position its balloon end across the lesion prior to inflation of the balloon and dilation of the stenosis.

Though successful at opening stenotic lesions, these dual lumen catheters are relatively bulky and stiff, which makes their use difficult for any lesions except those that are proximal and localized in nontortuous, easily accessible vessels. Moreover, these over-the-wire balloon catheters of early design require an additional implanting physician or assistant to control the guide wire during positioning of the assembly because catheter and wire movement are independent of one another. This complex coordinated activity requires both experience and skill and may result in a slower insertion procedure than desired.

An alternative conventional over-the-wire catheter assembly utilizes a non-removable guide wire that allows for longitudinal or axial movement. However, this design has a significant drawback because the entire non-removable guide wire catheter assembly must be removed to accomplish replacement or exchange of the balloon. In some cases of PTCA it is necessary to replace the balloon with one of different diameter or configuration following the initial dilation.

Additionally, cases of acute reclosure have been noted where the lesion recloses following dilation and removal of the balloon catheter. One response to this reclosure problem has been the placement of an expandable stent into the artery at the lesion with another replacement balloon catheter. This alternative system increases the difficulties of these subsequent procedures by requiring that the replacement catheter renegotiate the entire placement path without the advantage of a guide wire.

A "monorail" variant of the standard balloon-over-a-wire system also has been developed where only the distal portion of the balloon catheter tracks over the guide wire. This system utilizes a conventional inflation lumen and a relatively short guiding or through lumen at the distal end. Its principal benefits are the reduction of frictional drag over the length of the externally located guide wire and the ease of balloon exchange. It provides the ability to recross an acutely closed vessel or to exchange balloons without removing the guide wire. However, a disadvantage of this "mono-rail" design is the increased difficulty in steering the guide wire because the guide wire is not supported by the balloon catheter. Additionally, the dual lumen distal design produces a larger profile and shaft size.

Another innovation in dilatation catheter design which is now conventional is the "fixed-wire" or integrated "balloon-on-a-wire" dilatation catheter. These single lumen designs utilize a relatively narrow wire positioned within the inflation lumen and permanently fixed to the distal end of the balloon. This construction produces a low-profile catheter assembly which is able to cross severely narrowed lesions and to navigate tortuous vascular pathways. Additionally, the fixed guide wire bonded at the distal end of the balloon improves the steerability and pushability of these designs which enhances their maneuverability. The thin shaft design also improves coronary visualization and enables all but the tightest critical lesions to be crossed.

However, though able to provide relatively quick and simple balloon placement as well as providing access to lesions otherwise unsuitable for PTCA, fixed-wire balloon-on-a-wire systems sacrifice the ability to maintain guide wire position across the lesion when exchanging balloons or the safety advantage of being able to recross an acutely closed vessel without repositioning the entire assembly.

Additionally, conventional dual balloon catheters are known which provide for a pair of dilatation balloons of graduated size, or which provide one balloon which is a dilatation balloon while a second balloon is spaced away from the dilatation balloon. These catheters are used subsequent to the artery dilation with the two balloons both serving as occlusion balloons to isolate a section of the artery including the lesion under treatment between the two inflated balloons. An additional lumen of the catheter communicates with the isolated space between the balloons so the lesion can be treated with therapeutic fluids supplied via this additional lumen. Yet another balloon may be provided in this isolated space to assist in driving the therapeutic material into the tissue of the lesion by pressurizing the isolated intraarterial space or by physically pressing outwardly into engagement with the walls of the artery.

Of course, these conventional multi-lumen, multi-balloon catheters are high-profile devices. That is, the complexity of the structure of the catheter with two or more balloons, and two or more lumens communicating with the balloons and other features of the catheters, results in a rather large diameter for these devices.

Accordingly, it is an object of the present invention to provide a balloon-on-a-wire dilatation or embolectomy catheter which incorporates all of the benefits of a small diameter fixed wire system yet allows for removal, reengagement or replacement of the balloon while leaving the guide wire in place to preserve an easily renegotiated path along the blood vessel being treated.

It is an additional object of the present invention to provide an integrated-wire dilatation or embolectomy catheter offering an extremely low profile and a small shaft size to facilitate maneuverability and placement of the catheter as well as to provide it with the ability to negotiate tortuous vessels and to pass highly stenosed lesions.

It is a further object of the present invention to provide an integrated-wire balloon catheter having a steerable guide wire releasably fixed inside the catheter to provide enhanced torqueability, pushability, and maneuverability in order to facilitate the rapid, single operator placement and positioning of the assembly.

Still additionally, it is an object of the present invention to provide a dual balloon catheter with only a single lumen, and which includes an infusion section intermediate of the two balloons.

Further, it is an object of this invention to provide a single lumen catheter of the type outlined above which includes valving structure responsive to axial movement of the guide wire for selectively allowing inflation of a dilatation balloon, a distal vent to be opened, or inflation of both the dilatation balloon and an occlusion balloon along with infusion of therapeutic material into an isolated space between the two balloons, which material also provides the inflation pressure for the two balloons.

SUMMARY OF THE INVENTION

These and other objects of the present invention are achieved by the low-profile, single-lumen, dual-balloon catheter with integrated guide wire which, in accordance with broad structural aspects thereof, includes at least a single-lumen catheter with a pair of axially spaced balloon sections, a seal and infusion portion between the two balloon sections, a seal portion at its distal end, and a guide wire assembly including a valving portion which sealingly engages either of the two seal sections, or engages neither of the seal sections to open a distal vent port communicating with the distal seal portion. The valving portion of the guide wire assembly includes at least one sleeve-like valve member which is rotatably carried on and axially movable with a core portion of the guide wire assembly. The sleeve-like valve member is sealingly receivable into and through either one of the seal sections of the catheter. This unique construction allows rotational and longitudinal movement of the guide wire relative to the remainder of the catheter where desired and, if necessary, allows the tubular shaft of the catheter to be removed and reengaged or fully exchanged over the guide wire.

More specifically, the flexible guide wire of the present invention preferably is formed of metal, polymeric material or a combination of both and is provided with a relative small cross-sectional diameter to increase its flexibility and to reduce the overall cross-sectional profile of the dilatation catheter assembly. The valving portion of the guide wire assembly preferably includes two spaced apart sleeve-like valve members, either one of which is sealingly receivable into either one of the seal sections of the catheter, but which in use of the catheter are employed with a respective one of the seal sections. This construction increases the flexibility of the catheter while also decreasing the axial movement of the guide wire which is necessary to effect a selected change in operating mode for the catheter. Also, the two valving members allow convenient placement of radiopaque indicia on the shaft and guide wire assembly which facilitates axial relative placement of the selected one of the two valve members in sealing engagement with a seal section of the catheter, or positioning of the guide wire assembly so that the distal port of the catheter is in communication with the single lumen.

In this manner, the present invention combines the functions of balloon dilation, dual balloon isolation of an intra-arterial or intra-vascular or intra-tubular space, infusion of the isolated space, and fluid communication to a distal vent port of the catheter from the single lumen thereof, as well as guide wire transmittal in a single lumen as opposed to the conventional multi-lumen balloon catheter designs. This unique construction provides an exchangeable balloon catheter having an exceptionally small insertion profile and all of the advantages previously associated with non-exchangeable fixed-wire catheters; yet it also provides the advantage of the ability to leave its guide wire in position across a lesion during balloon exchange or removal. Because of the multiple functions which can be performed with the present catheter, however, removal of the catheter and its replacement with a second or subsequent catheter to perform initial or subsequent therapeutic treatment will be reduced. Thus, trauma to the patient may also be reduced by use of the present invention. The time required for lesion treatments may also be reduced because the number of catheter replacements required may be reduced or eliminated.

To facilitate visualization of the guide wire and balloon catheter during use the apparatus of the present invention is preferably provided with one or more radiopaque markers. Typically, these markers are formed of small coils, strips or spheres of gold, platinum or other dense, relatively inert metal. In one embodiment of the present invention a radiopaque spring coil of flexible wire is provided proximally to the valving portion of the guide wire assembly. Similarly, a radiopaque marker is located along the shaft of the catheter. When these two markers are disposed in a first axially spaced relative position the single dilatation balloon is inflatable. When the two markers are moved into a second position of congruence with one another by axial relative movement of the guide wire assembly, the distal vent port is communicated with the single lumen of the catheter. And when the markers are disposed in a third axially spaced relative position with their positions reversed from the first position, the dilation and occlusion balloon are both inflatable, while the axial space between these balloons is communicated to the single lumen of the catheter via the infusion portion.

It is also contemplated as being within the scope of the present invention to position radiopaque markers on the balloon catheter to enable the physician to visualize the placement of the balloon relative to the guide wire and target lesion or site.

Other features and advantages of the present invention will become apparent from the following detailed description, taken in conjunction with the accompanying drawings which illustrate, by way of example, the principles of the present invention.

DETAILED DESCRIPTION

Figures 1, 2:
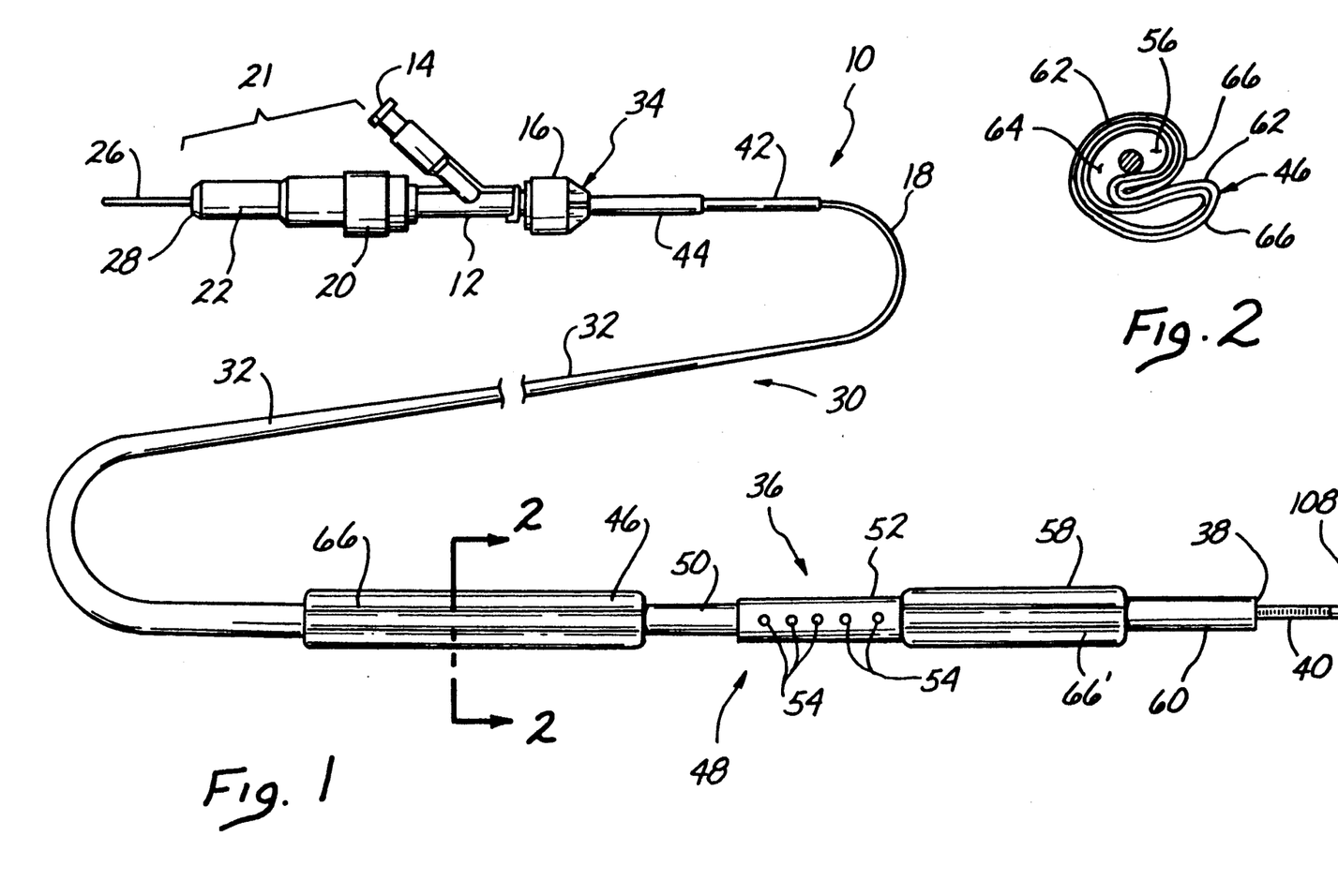
FIG. 1 is a fragmentary view in elevation of a low-profile single-lumen dual-balloon catheter with integrated guide wire for dilatation/occlusion and drug infusion illustrating the principles of the present invention.
FIG. 2 is an enlarged cross-sectional view of a balloon portion of the catheter of FIG. 1.

Referring more particularly to the drawings in which similar elements are indicated by identical reference numerals, FIG. 1 shows a single-lumen catheter, generally referenced with the numeral 10. The foreground portion of FIG. 1 is rendered at a larger scale than the background portion of this figure to better depict the structure of the catheter 10. The catheter includes a Y-connector 12 which is provided with an inflation port 14 and a compression hub 16 for sealing a catheter body 18 to Y-connector 12. A drum device 20 located at the proximal end of connector 12 is capable of hemostatically sealing the guide wire and catheter from inflation pressure. This drum device 20 is provided with a torque assembly, referenced with the numeral 21. Torque assembly 21 internally includes a pin-vise 22 for securely holding a guide wire assembly (hereinafter generally referenced with the numeral 24, and which is further described below) of the catheter 10. The pin vice 22 is preferably held internally to the two-part torquer. The seal is controlled by the drum device 20. Guide wire 24 is releasably held by the pin-vise 22 of the torquer. The torquer 21 provides the physician with the ability to rotate the guide wire 24. A proximal portion 26 of the guide wire assembly is seen extending outwardly of the vice 22. At 28 the torquer assembly 21 is provided with a torque cap. Preferably, the cap 28 is adjustable or releasable as this facilitates the removal or exchange of the catheter.

Although not essential to the practice of the present invention, the torquer 21 of Y-connector 12 provides a physician with the ability to rotate the catheter guide wire assembly 24 via its proximal portion 26 which is clamped in pin-vise 22 in order to steer the advancing catheter through the desired vascular or body pathway without assistance from other guidance devices. Additionally, as will be discussed in detail below, Y-connector 12 effectively seals the proximal end of the catheter to maintain working pressure therein while allowing rotational inputs from the physician to be directed to the guide wire.

An exemplary embodiment of the low-profile single-lumen dual-balloon catheter with integrated guide wire of the present invention is shown generally as reference 30 in FIG. 1, and is secured to compression hub 16 of Y-connector 12. This catheter 30 includes a flexible elongated tubular shaft 32 having a proximal end 34 secured in the compression hub 16, and a distal end portion 36 terminating at a distal end 38. The guide wire assembly 24, including proximal portion 26, extends entirely through the shaft 32, and includes a flexible coil termination portion 40 extending axially beyond the distal end 38 of the shaft 32. Flexible tubular shaft 32 is preferably formed of a polymeric material such as polyethylene, polyamide, polyimide, polypropylene, polyvinylchloride, polyester such as polyethyleneterephthalate (PET), or polyolefin copolymer. Additionally, to improve its lubricity, shaft 32 may be coated with PTFE, silicone or other materials including low friction lubricants. As shown in FIG. 1, proximal end 34 of shaft 32 may be provided with additional protective sleeves 42 and 44 to strengthen the junction of shaft 32 to Y-connector 12 and prevent kinking of the shaft during manipulation and placement of catheter 30.

Distal end portion 36 of shaft 32 includes a number of elements which are sequentially arranged axially along the length of the catheter 30 in this end portion 36. First adjacent to the remainder of the shaft 32 is a proximal expandable dilatation balloon 46 (shown deflated), the details of which are more readily apparent in the enlarged cross section of FIG. 2. Next to the proximal dilatation balloon is a waist portion 48 which includes both a cylindrical seal section 50, and a slightly larger diameter perforate infusion section 52. The perforate infusion section 52 defines at least a single perforation 54 opening outwardly from the single lumen of the catheter 30 (which single lumen is not seen in FIG. 1, but which will be generally referenced with the numeral 56 hereinafter) on the waist portion 48. According to the exemplary embodiment of the invention as depicted, the infusion section 52 includes a plurality of perforations 54 spaced axially along the catheter 30 in the waist portion 48 as well as being circumferentially arrayed around the infusion section 52.

Next adjacent to the waist portion 48 is a distal expandable occlusion balloon 58. This occlusion balloon 58 is next to a distal seal section 60 which terminates at distal end 38. As illustrated, the distal end 38 of catheter 30 is open axially, and the distal coil termination portion 40 of the guide wire assembly 24 extends from this end 38 of the shaft 32 to extend the catheter 30 somewhat beyond the distal portion 36 of the shaft portion 32.

Figure 3:
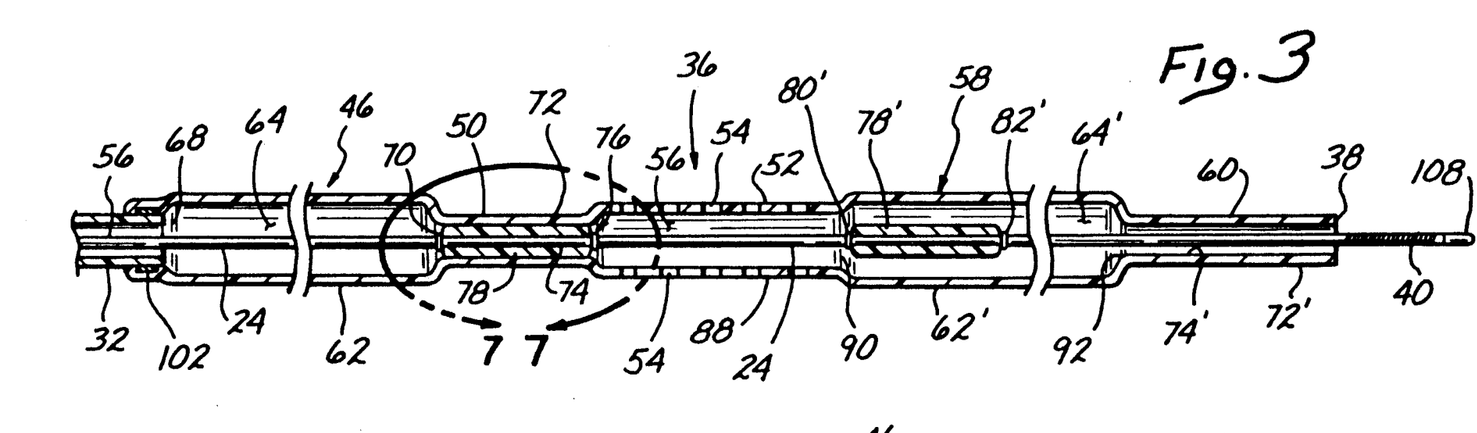
FIG. 3 is a partial longitudinal cross sectional view of the distal portion of the balloon catheter of FIG. 1 shown in a collapsed operative position.

Viewing FIGS. 2 and 3 in conjunction, and considering first the cross section of FIG. 2, an exemplary deflated and collapsed or folded proximal dilatation balloon 46 is illustrated. Both the proximal dilatation balloon 46 and the distal occlusion balloon 58 are essentially the same so far as their basic structure is concerned when seen in cross section. Accordingly, the description herein of the balloon 46 will suffice also to describe balloon 58 to the same extent, a prime being added to the reference numeral when reference is made to the latter balloon. The balloon 46 is seen to include a side wall 62 which is folded and wrapped over on itself to provide a comparatively small overall diameter when deflated. The guide wire assembly 24 passes through a respective portion 64 of the single lumen 56 of the catheter 30, which portion is inwardly defined by the balloon 46 so that the wall 62 circumscribes and is supported by, as well as supporting, the guide wire assembly 24. As is easily seen, the side wall 62 outwardly defines longitudinal fold lines, generally referenced with the numeral 66. Because of this folded and wrapped over condition of the side wall 62, the side wall may be several layers thick over the guide wire assembly 24 in some locations while being only a single thickness over the assembly 24 in other locations. For simplicity of illustration, this multiple thickness of the side wall 62 in the collapsed condition of the balloons 46 and 58 is omitted from FIG. 3.

Preferably, the balloons 46, 58, infusion section 52, and seal sections 50, 60, are integrally formed of a single piece of material. Proximally of the balloon 46, the shaft 32 is bonded to a proximal orifice 68 of the balloon 46. Cooperatively, the shaft 32 and balloons 46, 58, infusion section 52, and seal sections 50, 60 define a single elongate lumen 56 extending throughout the length of catheter 30. Alternative constructions may be utilized so long as dilatation balloon 46 and occlusion balloon 58 are sealingly connected proximally and distally in the distal end portion 36 of tubular shaft 32. For example, balloons 46 and 48 may be formed as expanded portions of the tubular shaft 32.

Accordingly, dilatation balloon 46 and occlusion balloon 58 may be constructed of the same or different polymeric materials utilized in the construction of shaft 32. Similarly, low friction coatings such as a fluoropolymer (for example, PTFE), silicone, or hydrophilic materials and lubricants may be utilized to enhance the movement of all components of catheter 30 during angioplasty.

In the embodiment shown, balloon 46 is provided with respective proximal and distal orifices, 68 and 70, the former of which is coaxially aligned with lumen 56 of the shaft portion 32, and is adapted to receive and conduct guide wire assembly 24. The guide wire assembly, as mentioned above, extends throughout the length of balloon 46 and beyond distal orifice 70. Distal orifice 70 is adjacent to the waist portion 48 which is provided with seal means in the form of sleeve-like seal section 50. This seal section 50 includes a nonexpandable but resilient side wall portion 72 defining an inner surface 74 which is sealingly and releasably engaged by guide wire assembly 24 at a valving portion 76 thereof in a sealing relationship.

Figure 7:
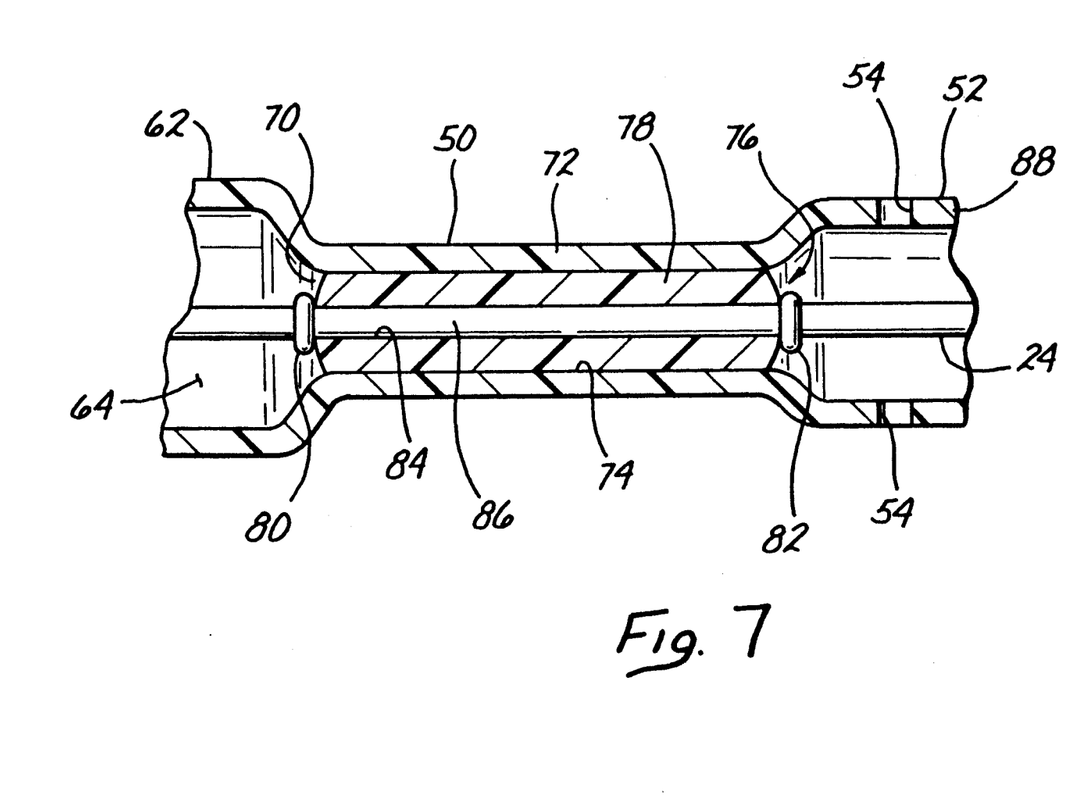
FIG. 7 is an enlarged cross sectional view of the balloon catheter of FIG. 3 taken in the encircled area referenced with the numeral 7.

Viewing FIGS. 3 and 7 in conjunction it will be seen that in the exemplary embodiment of the present invention the means of valving portion 76 of guide wire assembly 24 which releasably engages the sleeve-like section 50 in sealing relationship is formed as a sleeve-like cylindrical collar 78 which is dimensioned to slidingly and sealingly engage into the sleeve-like seal section 50 with a light friction fit. That is, the collar 78 will pass through the seal section 50, in response to either a sufficient pulling or pushing force on guide wire assembly 24, but the collar 78 does not simply fall or slip through the seal section 50. This cylindrical collar 78 is sealingly and relatively rotatably coupled to guide wire 24, but is constrained from relative axial movement on the guide wire assembly 24 by a pair of retaining rings 80 and 82 respectively carried immovably on the guide wire assembly 24 proximally and distally of the collar 78. The retaining rings 80 and 82 may be welded or swaged onto the guide wire assembly 24, for example. Alternatively, a stepped diameter on the guide wire assembly 24 may be used to define a shoulder against which the collar 78 engages at one side thereof to axially locate this collar relative to the guide wire assembly. A single retaining ring 80, 82 would then suffice to axially locate the collar 78.

The sealing relationship of the collar 78 on the guide wire assembly 24 is established by the sealingly close fit of a cylindrical bore 84 through the collar member 78 on a cylindrical surface portion 86 of the guide wire assembly 24. Because the collar member 78 is relatively long in relation to the diameter of the bore 84, and the fit between the bore 84 and surface 86 is close, fluid leakage axially through bore 84 is minimal. However, the fit of collar member 78 on surface portion 86 of the guide wire assembly is such that the latter is substantially freely rotatable relative the collar member.

Resilient sleeve-like seal section 50 may be formed from the same material forming the remainder of tubular shaft 32, or it may alternatively be formed from a lubricous polymeric material. Preferably, sleeve 50 is formed of the same material and is integral with balloon 46. Alternatively, resilient sleeve 50 may be coated along its inner surface with a lubricous material to facilitate its engagement with cylindrical collar 78. Cylindrical collar 78 similarly can be formed of a wide variety of materials ranging from stainless steel to polymeric materials and may even be formed as an integral part of guide wire assembly 24. However, it is preferred that collar 78 be formed of a polymeric material such as PVC, polyamide, polyimide, or fluoropolymer such as polytetrafluoroethylene (PTFE) as this provides an added degree of flexibility to the guide wire assembly 24 within the distal end portion 36 of the catheter 10.

This exemplary construction produces a releasably engaging seal which fixes guide wire 24 removably in position relative to balloon 46 yet allows guide wire 24 to be rotated freely without wrapping balloon 46 about the shaft 32 or guide wire 24. Additionally, while the retaining collars are shown in FIGS. 3 and 7 as being disposed immediately on each side of the collar 78, those ordinarily skilled in the pertinent arts will recognize that these collars 80 and 82 may be spaced somewhat from the collar 78 so that an added degree of sliding axial movement for the guide wire assembly 24 is provided without dislodging the sleeve-like collar from sealing relation with the seal section 50. This added degree of axial movement allows the positioning physician to extend or retract the distal end portion 40 of guide wire assembly 24 relative to the distal end portion 36 of the catheter shaft 32 where necessary for steering and positioning of the catheter while still retaining the seal between collar 78 and seal section 50. As will be seen the collar 78 can be disengaged from the seal section 50 by axial movement of the guide wire assembly 24.

Still viewing FIG. 3, it is sen that the catheter 10 at waist portion 48 also includes the infusion section 52 defining a plurality of orifices 54. Particularly, the infusion section 52 includes a side wall 88 which defines the orifices 54 extending therethrough from the single lumen 56 to open outwardly on the infusion section 52. Importantly, the inner diameter of the lumen 56 within the side wall 88 is larger than that at surface 74 of seal section 50.

Distally of the waist portion 48, the distal occlusion balloon 58 includes a respective proximal and distal orifice, 90 and 92, both of which are coaxially aligned with lumen 56 of the shaft portion 32, and which are adapted to receive and conduct guide wire assembly 24. The guide wire assembly, as mentioned above, extends throughout the length of balloon 58 and beyond distal orifice 92. Distal orifice 92 is adjacent to the distal seal section 60. Like the seal section 50, the seal section 60 includes a side wall, referenced with the numeral 72', which defines an inner surface 74'. In nature of construction, materials of construction, and dimension of their inner diameter at the surfaces 74 and 74', the seal sections 50 and 60 are similar. The distal seal section 60 leads to and terminates at the distal end 38. At this distal end 38, the side wall 72' defines a distal end port 94 from which the distal coil termination portion 40 of the guide wire assembly 24 projects distally.

The valving portion 76 of the guide wire assembly 24 is further provided with seal means in the form of sleeve-like collar 78'. That is, the means of valving portion 76 of guide wire assembly 24 which may releasably engage the sleeve-like seal section 60 in sealing relationship is formed as a sleeve-like cylindrical collar 78', which is retained axially (with relative rotation being allowed) by a pair of retention collars 80' and 82', and which is dimensioned to slidingly and sealingly engage into the sleeve-like seal section 60 with a light friction fit. In the depicted position of the guide wire assembly 24, the sealing collar 78', is spaced from the seal section 60. Distally of the collar 78', the guide wire assembly 24 defines a diameter which is smaller than the collar 78'. Consequently, in the depicted relative position of the guide wire assembly 24, the infusion section 52 of waist portion 48, as well as the distal balloon 58 are open to ambient distally through the open distal end port 94.

Figure 4:
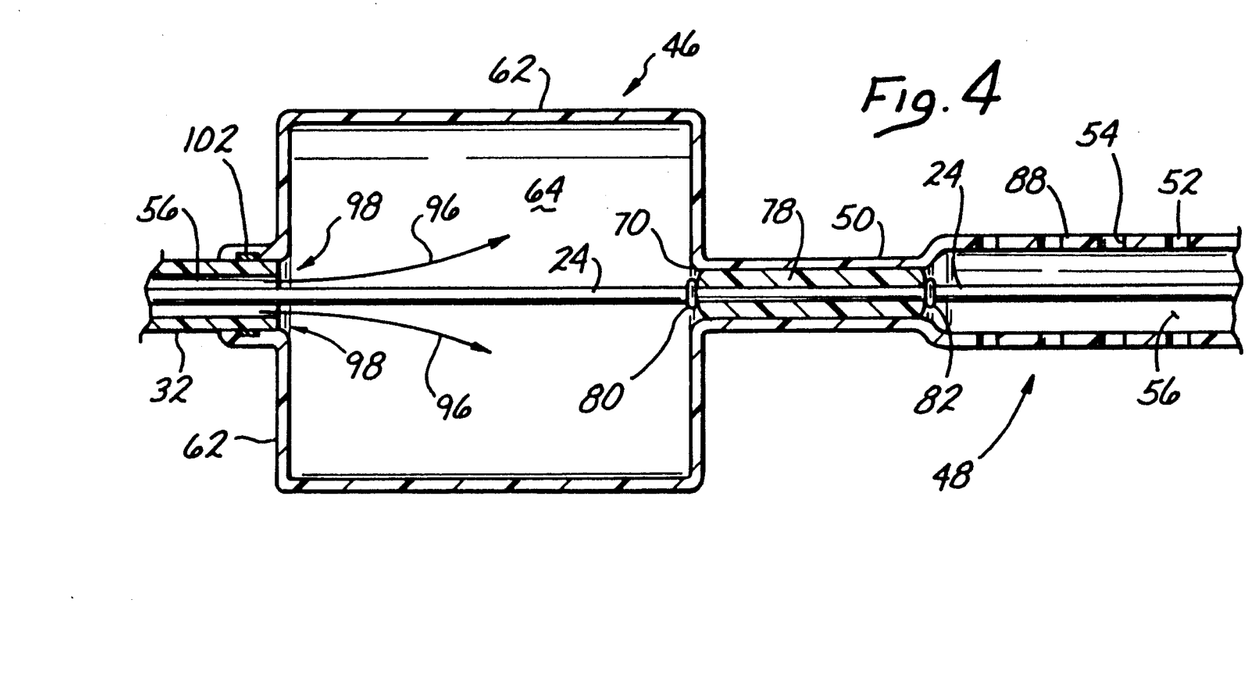
FIG. 4 is a partial cross sectional view similar to FIG. 3, and showing a part of the catheter in an alternative inflated operative position.

In FIG. 4 balloon 46 has been inflated by a radiologically opaque or partially opaque contrast fluid, the inflow of which into the balloon 46 from shaft 32 via orifice 68 is depicted by arrows 96. The radiopaque fluid allows the attending physician to view that the balloon is inflated in the correct location with respect to a vascular or arterial lesion, stenosis or other blockage. Also, as the dilatation balloon inflates, this enlargement in diameter of the balloon is visible to the physician who can thereby judge the extent to which the vessel or body structure is being enlarged. In the position of guide wire assembly 24 depicted in FIGS. 3 and 4, the orifice 70 is sealingly closed by the collar member 78 in seal section 50. Consequently, the balloon 46 is inflated by the contrast fluid supplied thereto. By way of example only, the initial or uninflated diameter of balloon 46 may be on the order of about 1 mm, and its inflated diameter may be from about 1.5 mm to about 5 cm. Thus, the balloon 46 may provide a ratio of diameter increase to its inflated condition which is from 1.5:1, to as much as 50:1.

Subsequent to the inflation of dilatation balloon 46, the contrast fluid is withdrawn as depicted by arrows 98 to deflate this balloon to its configuration seen in FIGS. 1-3. At this time, while the catheter 10 is visible to the physician because of the radiopaque markers 102, 40 fluid therein, the catheter 10 is preferably retracted slightly so that the balloons 46 and 58 straddle the lesion which has just been dilated.

Figure 5:
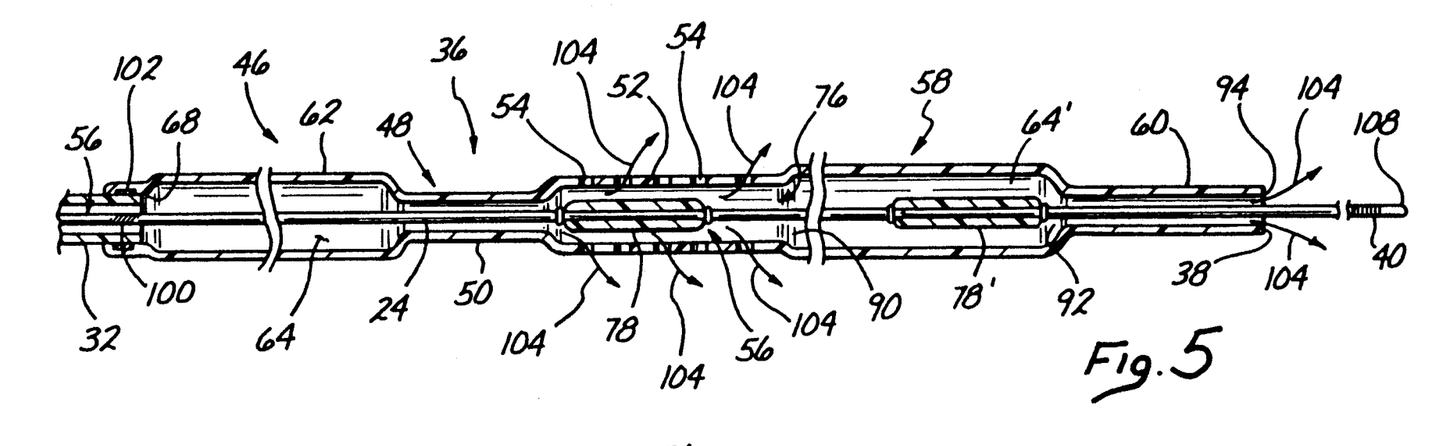
FIG. 5 is an enlarged partial cross sectional view of the distal portion of the catheter shown in an alternative collapsed operative position.

FIG. 5 shows that the guide wire assembly 24 is subsequently advanced axially relative to the remainder of the catheter in order to open orifice 68 to distal end port 94. In order to visually indicate that the orifice 68 is open, a radiopaque marker 100 carried on the guide wire assembly 24 and which in the position of the guide wire assembly 24 seen in FIGS. 1-4 was leftwardly of a marker sleeve 102 proximal of the balloon 56, is moved axially into congruence with this sleeve. In other words, the attending physician advances the guide wire assembly 24 so that the two spaced apart visual indications provided by the markers 100 and 102 merge. This visual merger indicates that the marker 100 is within or immediately adjacent to the marker 102. Thus, the collar 78 is moved from within to a position spaced from the seal section 50, and the collar 78' is moved toward but short of the seal section 60. This opening of fluid communication through the lumen 56 and from the distal end port 94 allows the contrast fluid still resident in the catheter 10 to be flushed therefrom, as is indicate by arrows 104 on FIG. 5, and to be replaced with a treatment fluid, for example, with an anti-proliferative drug such as heparin introduced via the Y-connector 12.

After the catheter is so repositioned and flushed, the guide wire assembly 24 is further advanced to bring the collar 78' into sealing engagement with the seal section 60. This sealing engagement of the collar 78' with seal section 60 may be indicated by the resistance to advancement of the guide wire which will be experienced because of the light frictional engagement of the collar member with the inner surface 74' of the seal section 60. However, preferably a second radiopaque marker 106 carried on the guide wire assembly 24 is brought into congruence with the marker sleeve 102. When the visual indications provided by the markers 102 and 106 as they merge, the attending physician can be sure that the collar 78' is sufficiently engaged sealingly into the seal section 60 that the orifice 92 is closed.

Figure 6:
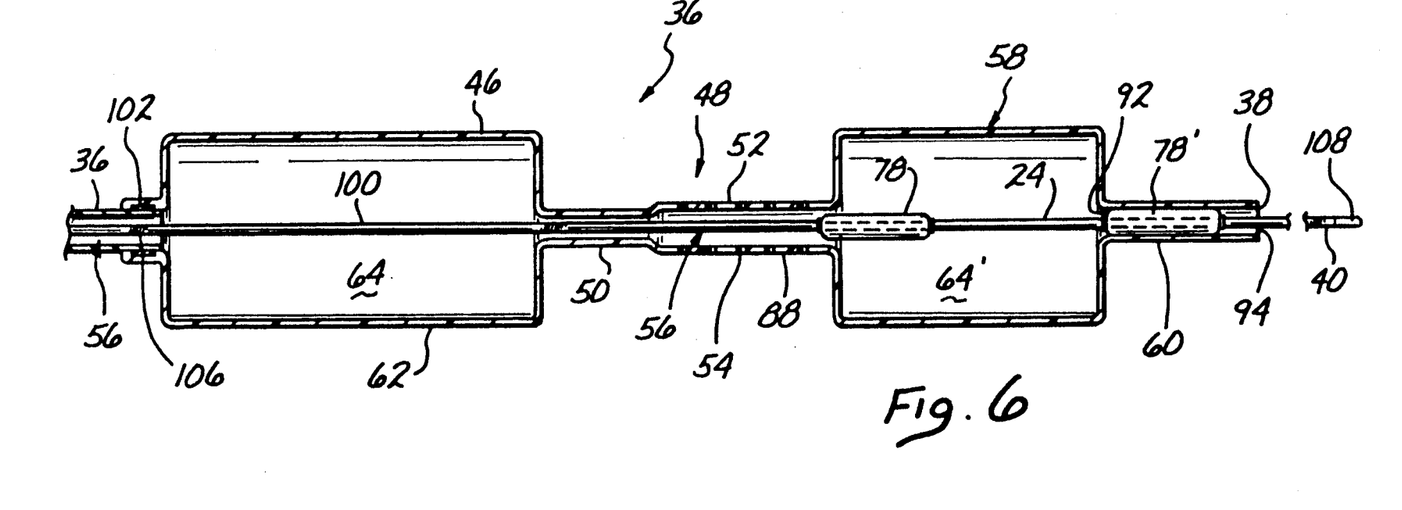
FIG. 6 is an enlarged cross sectional view of the distal end portion of the catheter illustrating an alternative inflated operative position of the catheter.

Consequently, further delivery of treatment fluid into the catheter 10 causes the two balloons 46 and 58 to both inflate, as is depicted in FIG. 6. This inflation of the balloons 46 and 58 causes them to substantially sealingly engage respective portions of the arterial or vascular wall (not seen in the drawings) to isolate therebetween an intraarterial or intravascular space including the lesion under treatment. That is, both the dilatation balloon 46 and occlusion balloon 58 serve in an occlusion mode to isolate the lesion therebetween. Because the waist portion 48 is open at infusion section 52, the infused treatment fluid is delivered to the lesion in high concentration. Also, systemic toxicity which may result if treatment drugs are simply delivered to the body as a whole is avoided because the target space is isolated from the remainder of the patient's circulatory system. After the treatment fluid has had a sufficient residence time in the target space between the balloons 46 and 58, most of this fluid may be aspirated out of the artery via the lumen 56, if desired. Of course, relief of the pressure on the treatment fluid, or aspiration of this fluid, results in the two balloons 46 and 58 collapsing substantially to their positions shown in FIG. 1 for removal of the catheter 10 from the patient. Alternatively, for an embolectomy type procedure the catheter can be withdrawn with the balloons inflated.

It is important to note that as shown in FIGS. 3 and 7, it is preferred that all portions of guide wire assembly 24 proximal to its valving portion 76, which has an enlarged diameter formed by cylindrical collars 78 and 78', have a cross-sectional diameter smaller than that of the outer diameter of these collars. This construction allows the balloon catheter of the present invention to be completely advanced or retracted along the entire longitudinal extent of guide wire assembly 24 for the purposes of balloon manipulation, removal or replacement. Thus, the balloon catheter can be replaced with a catheter having a balloon provided with a different expandable diameter if necessary to reopen a particularly difficult stenotic lesion. Similarly, if problems develop with the inflation of balloons 46 and 58 during angioplasty it is possible to replace the balloon with a properly functioning device. All the physician need do is to retract catheter 30 along guide wire assembly 24, leaving this guide wire assembly in position across the target lesion. Subsequently, a replacement catheter can be advanced along the positioned guide wire without having to retrace the entire vascular pathway. As those skilled in the pertinent art will appreciate, this placed guide wire greatly facilitates the speed and safety of such a catheter replacement procedure.

It also should be emphasized that axial lumen 56 of the present invention is configured to perform a triple role. As shown in FIG. 3, the diameter of axial lumen 56 is greater than that of guide wire assembly 24 everywhere except at the sealing sections 50 and 60, and the valving portion 76 with collars 78 and 78'. By virtue of this construction, axial lumen 56 is adapted to both receive guide wire assembly 24 and to conduct an inflation fluid to and from balloons 46 and 58. Further, the balloon 46 can be inflated alone, or with the balloon 58. In this latter mode of inflation, the infusion section 52 also serves to deliver a treatment fluid to an isolated arterial space. This multifunctional catheter design produces an ultra-low profile device which significantly enhances its ability to cross very tight stenoses or to traverse particularly difficult vascular pathways.

As an additional benefit, relative to the conventional and larger-diameter balloon catheters presently known, larger volumes of radiographic visualization dyes may be injected about tubular shaft 32 to enhance its visibility during placement of the apparatus. Thus, the ease and precision of placement of the present catheter over the known devices may be improved.

Along these lines, exemplary non-limiting dimensions for the balloon catheter assembly of the present invention may be as follows. For example, as is typical in the coronary arts, the overall length of catheter 30 will typically range from 120 cm to 160 cm. The axial length of each of the dilatation balloon 46 and occlusion balloon 58 will comprise approximately 0.5 cm to 4 cm of this overall length. Typically, dilatation balloons are available in stepped dilation diameters ranging from approximately 1.0 mm to 5.0 mm in 0.5 mm or 0.25 mm increments. As known in the art, these inflation diameters are typically achieved at 6 to 10 atmospheres of pressure. Naturally, the deflated profile of the dilatation balloons increases slightly with the final dilation diameter. However, while the majority of prior art balloon catheters have a deflated balloon profile measuring approximately 0.04 inches in diameter, the balloon catheter of the present invention has a typical dilated balloon profile of only about 0.03 inches, or less than 1 mm. Similarly, the multifunctional, single-lumen design of the present invention produces a tubular shaft 32 having a correspondingly narrow profile.

Exemplary non-limiting diameters for the proximal portion of guide wire 32 range from 0.005 to 0.016 inches whereas the preferred exemplary outer diameter for both of the cylindrical collars 78 and 78' ranges from approximately 0.012 to 0.020 inches. Thus, in the embodiments of the present invention illustrated in the drawing FIGS., the distal end portion 40 of guide wire assembly 24 is provided with a cross-sectional diameter on the order of approximately 0.014 inches. Cylindrical collars 78 and 78' are formed of a polymeric material such as PTFE having an outer diameter of approximately 0.016 inches and a wall thickness of approximately 0.005 inches. It should be emphasized that the proximal diameter of guide wire assembly 24 need not be constant and may taper to provide an enhanced degree of flexibility toward the distal end of the guide wire assembly. Guide wire assembly 24 itself is preferably formed of metal such as stainless steel but also may be constructed of polymers or polymer coated metals as is known in the art. An exemplary overall wire length for guide wire assembly 24 is on the order of 175 cm. The cross section of guide wire assembly 24 proximal to cylindrical collar 78' need not be circular to be within the scope of the present invention. For example, generally elliptical or ribbon-like configurations may be utilized to provide an enhanced degree of flexibility.

Although not essential to the practice of the present invention, guide wire assembly 24 is preferably provided at flexible distal spring coil 40 with a smooth hemispherical radiopaque tip 108. This tip 108 presents a rounded distal end for the guide wire assembly 24 in order to reduce vascular trauma as guide wire assembly 24 is advanced along a vascular pathway. Spring coil 40 may be formed of any resilient material, preferably metal, and in the preferred embodiment of the present invention is formed of a radiopaque material such as platinum or gold. Thus, spring coil 40 with tip 108 functions as an additional marker to assist the physician in positioning the apparatus of the present invention.

Though spring coil 40 is illustrated in the drawing Figs. as being relatively straight, it is commonly known in the art to precurve spring coil 40 so that the implanting physician can rotate wire assembly 24 and direct tip 108 of wire coil 40 into specific vascular junctions to direct the entire assembly along the proper pathway. Preferably, the physician can manually apply a specific curve to the coil 40 based on his preference. Rotational manipulation of wire 24, or "torquing" as it is referred to in the art, is accomplished by rotating torquer 21 of Y-connector 12 which firmly clamps wire 24 at proximal portion 26 in pin-vise 22.

The axially flexible construction of guide wire 24 transmits this torque along the entire longitudinal extent of wire 24 to coil 40. However, because cylindrical collars 78 and 78' are preferably sealingly coupled to guide wire 24 in a relatively rotatable manner, this torque is not transmitted to balloons 46 and 58, and prevents these balloons from wrapping in a spiral fashion around guide wire 24. Alternatively, where cylindrical collars 78 and 78' are not relatively rotatably fixed for axial movement with the guide wire assembly 24, it is preferred that the outer surface of these cylindrical collars 78 and 78' be very smooth to allow a certain degree of slippage between them and seal portions 50 and 60. In this manner, balloon wrapping also can be prevented.

As noted above, the exchangeable integrated-wire balloon catheter of the present invention enables a physician to exchange one catheter for a second catheter along the pre-positioned guide wire without having to retrace the entire vascular pathway with the guide wire. As those skilled in the art will appreciate, replacement catheters produced in accordance with the teachings of the present invention need not include a guide wire assembly.

Thus, the apparatus of the present invention provides an exchangeable integrated-wire balloon catheter that can be positioned by a single physician. Because the apparatus of the present invention provides the maneuverability of a fixed-wire catheter coupled with the benefits of an ultra-low catheter profile it can be quickly and easily maneuvered into position across lesions that are critically narrowed and irregularly shaped. Following expansions of the dilatation balloon and dilation of the lesion, the catheter of the present invention can be slightly repositioned to function in an occlusion mode for administration of treatment fluid to the lesion.

Further, the distal end of its guide wire may be left in place and the shaft of the catheter may be retracted back from the lesion to allow the physician to visualize blood flow while retaining the guide wire access across the lesion. If necessary, the physician can advance the catheter and reengage the valving portion of the guide wire to reseal one or both of the balloons for purposes of reinflation.

Alternatively, while leaving the guide wire in place the physician can completely remove and replace the balloon catheter with one having alternative dimensions which, in turn, can be sealingly engaged with the distal end of the guide wire for inflation purposes or a conventional over-the-wire catheter may be advanced along the wire. Lastly, in cases of acute reclosure the guide wire of the present invention can be utilized to direct a perfusion catheter into position.

In closing it is to be understood that the embodiments of the invention disclosed herein are illustrative of the principles of the invention and that other modifications may be employed which are within the scope thereof. Thus, by way of example, but not of limitation, one or both of the seal sections 50 and 60 may be configured to extend into the dilatation balloon as opposed to the depicted configuration in which these seal portions extend outwardly of the balloon portions. Accordingly, the present invention is not limited to that precisely as shown and described in the specification.

What is claimed:

1. A single-lumen dual-balloon catheter and guide wire combination for dilatation, occlusion, and infusion of treatment fluid, said catheter comprising:
    a flexible small diameter guide wire having a valving portion adjacent to a distal end thereof;
    a flexible elongated tubular shaft having a proximal end and a distal end portion terminating in a distal end, said distal end portion including an expandable proximal balloon and an expandable distal balloon spaced axially from said proximal balloon by a waist portion therebetween, a single axially extending fluid conducting lumen adapted to receive said guide wire extending through said shaft in fluid communication with each balloon, said waist portion defining at least one perforation opening from said lumen outwardly thereon, and both said proximal balloon and said distal balloon having a respective distal orifice coaxially aligned with said lumen and adapted to receive said guide wire, each of said distal orifices being provided with means for releasably engaging in sealing relationship with said valving portion of said guide wire.

2. The catheter of claim 1 wherein said means for releasably engaging in sealing relationship comprises:
    a resilient sleeve-like seal portion extending from said distal orifice and dimensioned to slidingly engage said valving portion of said guide wire, which valving portion is of relatively enlarged diameter.

3. The catheter of claim 1 wherein said enlarged diameter distal end valving portion of said guide wire comprises:
    a cylindrical sleeve-like collar member sealingly coupled to said guide wire.

4. The catheter of claim 3 wherein said collar member is relatively rotatably captured upon said guide wire with a selected relative axial movement permitted therebetween.

5. The catheter of claim 4 wherein said selected relative axial movement between said collar member and said guide wire is limited to substantially no axial movement therebetween.

6. The catheter of claim 3 wherein said cylindrical collar is formed of a polymeric material.

7. The catheter of claim 4 wherein said polymeric material is selected from the group comprising:
    polyvinylchloride, polyamide, polyimide and fluoropolymer.

8. The catheter of claim 3 wherein said cylindrical collar is formed of metal.

9. The catheter of claim 3 wherein said valving portion includes a pair of said collar members spaced axially apart on said guide wire.

10. The catheter of claim 1 further comprising at least one radiopaque marker disposed adjacent to said enlarged diameter distal end portion of said guide wire.

11. The catheter of claim 10 wherein said radiopaque marker comprises a flexible metallic coil extending beyond said enlarged diameter distal end portion of said guide wire.

12. The catheter of claim 1 further comprising at least one radiopaque marker fixed adjacent to the proximal end of said proximal balloon.

13. A low-profile single-lumen dual-balloon catheter for use in conjunction with a flexible, small diameter guide wire having a distal end valving portion of comparatively enlarged diameter, said catheter comprising:
   a flexible elongate tubular shaft having a proximal end and a distal end portion terminating at a distal end, and at least one axially extending fluid conducting lumen adapted to receive said guide wire extending therethrough; and
   an axially spaced apart pair of expandable balloons relatively located proximally and distally of one another in said distal portion adjacent said distal end of said tubular shaft in fluid communication with said lumen and each balloon having a respective distal orifice coaxially aligned with said lumen and adapted to receive said guide wire, said distal orifice of each balloon being provided with means for releasably engaging in sealing relationship said enlarged diameter distal end valving portion of said guide wire.

14. The catheter of claim 13 wherein said means for releasably engaging in sealing relationship comprises:
   a resilient sleeve-like seal section extending from said distal orifice and dimensioned to slidingly engage said enlarged diameter distal end valving portion of said guide wire.

15. The catheter of claim 13 wherein said elongated tubular shaft and at least one of said expandable balloons are formed of resilient polymeric material.

16. The catheter of claim 15 wherein said polymeric material is selected from the group consisting of homopolymers and copolymers of:
   polyvinylchoride, polyethylene, polyolefin, fluoropolymer, polyamide, polyester, polyimide, and polypropylene.

17. A low-profile single-lumen dual-balloon catheter and guide wire combination comprising:
   a flexible, small diameter guide wire having proximal and distal ends, with a valving portion of said distal end being of a larger diameter than the remainder of said guide wire;
   a flexible elongate tubular shaft having a proximal end and a distal end and a single axially extending fluid conducting lumen adapted to receive said guide wire extending therethrough; and
   a pair of axially spaced apart balloons each in fluid communication with said lumen and disposed in proximal and distal relative position, a waist portion of said catheter between said balloons including a perforate infusion portion having at least one perforation opening from said lumen outwardly on said catheter between said balloons, each one of said pair of balloons having a respective distal end coaxially aligned with said lumen and adapted to receive said guide wire, each of said distal ends being provided with means for releasably engaging said enlarged diameter distal end portion of said guide wire in sealing relationship.

18. The combination of claim 17 wherein said larger diameter guide wire distal end is defined by a cylindrical collar member coupled to said guide wire distal end for relative rotational movement and a selected axial relative movement.

19. The combination of claim 18 wherein said means for releasably engaging said enlarged diameter distal end portion of said guide wire is a resilient sleeve-like seal portion of said catheter extending from said distal end.

20. The combination of claim 19 wherein said elongated tubular shaft and said expandable balloon are formed of resilient polymeric material.

21. The combination of claim 19 wherein said resilient sleeve is formed from a lubricous polymeric material.

* * * * *